(12) United States Patent
Tamburino

(10) Patent No.: US 9,861,731 B2
(45) Date of Patent: Jan. 9, 2018

(54) ENDOLUMINAL DEVICES AND SYSTEMS FOR CREATING TWO-WAY BLOOD FLOW FOR THE TREATMENT OF HEART FAILURE

(71) Applicant: Corrado Tamburino, Cantania (IT)

(72) Inventor: Corrado Tamburino, Cantania (IT)

( * ) Notice: Subject to any disclaimer, the term of this patent is extended or adjusted under 35 U.S.C. 154(b) by 0 days.

(21) Appl. No.: 15/038,045

(22) PCT Filed: Sep. 25, 2014

(86) PCT No.: PCT/IB2014/064832
§ 371 (c)(1),
(2) Date: May 20, 2016

(87) PCT Pub. No.: WO2015/075576
PCT Pub. Date: May 28, 2015

(65) Prior Publication Data
US 2016/0296684 A1    Oct. 13, 2016

(30) Foreign Application Priority Data

Nov. 25, 2013    (IT) .............................. BS2013A0176

(51) Int. Cl.
*A61M 1/12*    (2006.01)
*A61M 1/10*    (2006.01)
*A61F 2/24*    (2006.01)
*A61B 17/00*    (2006.01)

(52) U.S. Cl.
CPC .......... *A61M 1/122* (2014.02); *A61M 1/1012* (2014.02); *A61M 1/1024* (2014.02); *A61M 1/1031* (2014.02); *A61M 1/1086* (2013.01); *A61M 1/1087* (2014.02); *A61B 2017/00575* (2013.01); *A61B 2017/00592* (2013.01); *A61B 2017/00597* (2013.01); *A61B 2017/00606* (2013.01); *A61F 2/24* (2013.01); *A61M 1/101* (2013.01); *A61M 1/1008* (2014.02); *A61M 1/125* (2014.02); *A61M 2205/32* (2013.01); *A61M 2205/3334* (2013.01); *A61M 2205/3341* (2013.01); *A61M 2205/3507* (2013.01); *A61M 2230/04* (2013.01)

(58) Field of Classification Search
CPC .................... A61B 17/00234; A61M 1/122
USPC ........................................... 604/9, 8
See application file for complete search history.

(56) References Cited

U.S. PATENT DOCUMENTS

| 2002/0173742 A1 | 11/2002 | Keren et al. |
| 2005/0148925 A1 | 7/2005 | Rottenberg et al. |
| 2005/0165344 A1 | 7/2005 | Dobak, III |
| 2013/0123569 A1 | 5/2013 | Gross |

FOREIGN PATENT DOCUMENTS

WO    2010128501 A1    11/2010

*Primary Examiner* — Carl H Layno
*Assistant Examiner* — Jon Eric C Morales
(74) *Attorney, Agent, or Firm* — Robert E. Alderson, Jr.

(57) ABSTRACT

Endoluminal devices are provided for the treatment of heart failure which include a central body adapted to permit the passage of interatrial blood, at least one anchor attached to the central body adapted to keep the endoluminal device in position within a defect present in the atrial septum of a patient's heart, and at least one control element engaged with the central body in a rotating manner. The rotation of the control element in relation to the central body creates a two-way flow of interatrial blood which allows the reduction of high pressure in the right side and in the left side of the heart.

12 Claims, 3 Drawing Sheets

ENDOLUMINAL DEVICES AND SYSTEMS FOR CREATING TWO-WAY BLOOD FLOW FOR THE TREATMENT OF HEART FAILURE

CROSS-REFERENCE TO RELATED APPLICATIONS

This application is a National Phase Application of PCT International Application No. PCT/IB2014/064832, International Filing Date, Sep. 25, 2014, claiming priority to Italian Patent Application No. BS2013A000176 (102013902210915), filed Nov. 25, 2013, each of which is hereby incorporated by reference in its entirety.

FIELD OF THE INVENTION

The object of the present invention is an endoluminal device and an endoluminal system for the treatment of heart failure, in particular for the creation of a two-way controlled flow of interatrial blood.

BACKGROUND OF THE INVENTION

The heart failure syndrome is a common pathophysiologic state in which the heart is unable to pump blood at a level appropriate to the requirements of the metabolizing tissues, or can it do so only with a high diastolic filling pressure. This clinical syndrome, which can be caused by various pathological conditions, is characterised by a low cardiac output and an increase in the intracardiac filling pressure.

Note that about one third of patients with heart failure suffer from diastolic heart failure whose symptoms are due, in most cases, to an increase in the pressure in the left atrium. This increase in the left atrial pressure causes an increase in the pulmonary venous pressure, a condition partly responsible for dyspnea. These symptoms include chronic dyspnea, a condition that worsens in the supine position causing small changes in the pulmonary venous pressure, resulting in an aggravation of symptoms. This condition may progress into pulmonary edema, one of the most dangerous consequences associated with the heart failure syndrome. Pulmonary edema is caused by the sudden increase in the capillary hydrostatic pressure and by the accumulation of fluid with low protein content in the interstitium and in the pulmonary alveoli. Without proper and prompt treatment, this condition can deteriorate rapidly and eventually lead to death.

As regards the right side of the heart, the pulmonary hypertension, a rare disease characterised by right ventricular failure and high right atrial pressure, can lead to systemic venous congestion and eventually to death. One of the therapeutic strategies adopted in the last stages of pulmonary hypertension is atrial septostomy, a percutaneous intervention aimed at reducing the high right atrial pressure by creating a hole in the native atrial septum. This procedure has been shown to be effective in increasing the cardiac output, improving the symptoms of heart failure and reducing the hyperactivity of the sympathetic autonomic nervous system.

Therefore, in the medical industry, the need is felt for devices and methods for the treatment of heart failure both as regards the right side and the left side of the heart.

SUMMARY OF THE INVENTION

The object of the present invention is to provide an endoluminal device and an endoluminal system for the treatment of heart failure which solves the drawbacks of the prior art keeping into account the needs of the field.

In particular, the object of the present invention is to provide an endoluminal device and an endoluminal system for regulating the amount of interatrial blood that flows from the left rightwards or from the right leftwards according to the atrial pressure.

Such objects are achieved by endoluminal devices and by endoluminal systems as described and claimed herein.

The features and advantages of endoluminal devices according to the present invention will appear more clearly from the following description, made by way of representative and non-limiting examples and with reference to the attached drawings.

DETAILED DESCRIPTION

Figure 1:
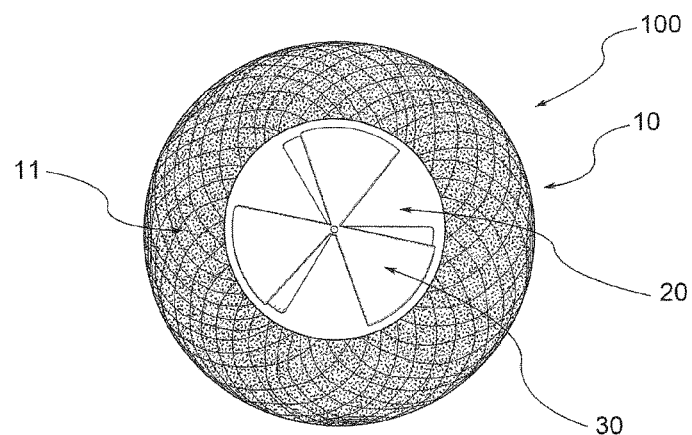
FIG. 1 shows a front view of an endoluminal device for the control of interatrial blood according to the present invention.
Figure 2:
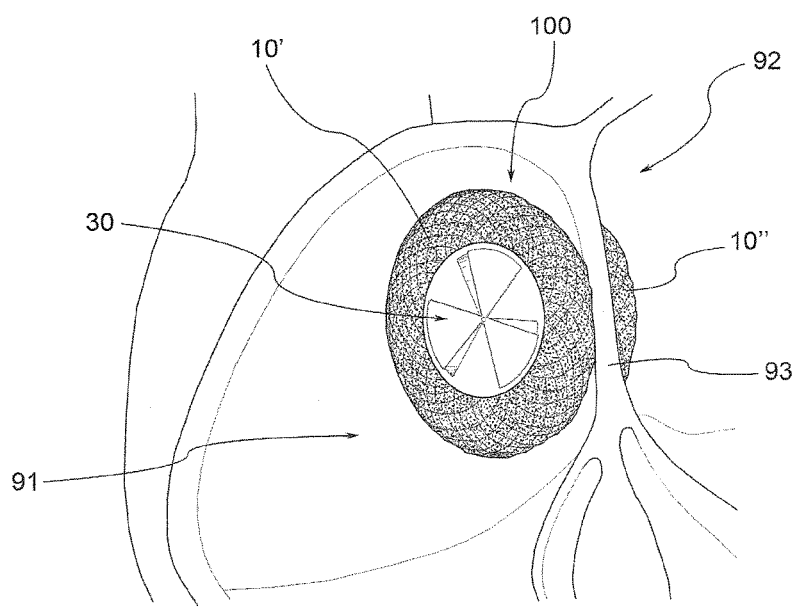
FIG. 2 shows the endoluminal device for the control of interatrial blood according to the present invention, positioned within the patient's heart.

With reference to the accompanying figures, and in particular to FIGS. 1 and 2, an endoluminal device 100 for the control of interatrial blood is shown.

The endoluminal device 100 comprises a central body 20, at least one anchor 10 adapted to keep the endoluminal device 100 in position within the patient's heart, and at least one control element 30 adapted to create a two-way controlled flow of interatrial blood.

As shown in FIG. 2, the endoluminal device 100 comprises a pair of anchors 10, each attached to one end of the central body 20.

The endoluminal device 100 is adapted to be positioned within the patient's heart, particularly in a dedicated hole made in the interatrial septum 93. During the delivery of the endoluminal device 100, a first anchor 10' is positioned in the left atrium 91 and a second anchor 10" is positioned in the right atrium 92, in such a way as to keep the endoluminal device 100 in position between the right atrium 92 and the left atrium 91.

In an alternative embodiment, anchor 10 is a substantially open link 11.

Link 11 is made of a material suitable for use in a patient, such as titanium, nitinol, stainless steel, Elgiloy®, MP35N®, Vitalium™, Mobilium™, Ticonium™, Platinorem™, Stellite®, tantalum, platinum or other elastic material. Alternatively, link 11 is made of polymeric material, such as PTFE, UHMWPE, HDPE, polypropylene, polysulfone, or other biocompatible plastic material. If a sufficiently elastic and resilient material is used, such as nitinol, link 11 is preformed into the desired shape, so that it can be temporarily elastically deformed to be fitted on a delivery catheter and then elastically recover the desired shape once positioned inside the patient's body.

Moreover, to improve the endothelialisation process, link 11 is provided with a covering layer made of bioabsorbable polymer, such as polylactic acid, polyglycolic acid, polycaprolactone, a combination of two or more of these bioabsorbable polymers, or it may be covered with a bioabsorbable fabric.

In an alternative embodiment, link 11 is made with a preformed wire, folded back on itself and attached in the desired shape by means, for example, of a welding or an adhesive. In case of welding, for example, a resistance welding technique or an arc welding technique are used, preferably in an inert gas and controlled cooling environment to control the grain structure in the point and around the welding site. In order to reduce the size of the grains and optimise the fatigue performance, the junction portions can be conditioned after welding by coining or forging.

In a further embodiment variant, link 11 is made from a hollow tube, drilled to form an open link, for example using laser cutting or water drill.

In an alternative embodiment variant not shown, the anchor is made from a plurality of flanges which extend radially outwardly from the central body 31. Preferably, the anchor includes two to eight flanges. In a variant, the flanges are positioned so as to define a gap (a space) between anchor 10' positioned on one side of the central body 20 and anchor 10" positioned on the opposite side. When the device is delivered, the flanges bend to accommodate the tissue of septum 93, which is positioned in the space between the two anchors. This gap is slightly less than the thickness of the interatrial septum 93, or greater than the thickness of the interatrial septum 93, or it is a negative gap, that is to say, the flanges on each side of the central body 20 intersect so as to exert a greater pressure on the interatrial septum 93.

Preferably, the flanges on one side of the central body 20 are staggered (not facing) with respect to the flanges on the opposite side, so that after placement of the endoluminal device 100, there are no pinching points, thereby reducing the risk of tissue damage.

Preferably, the material of anchor 10 has a greater flexibility than the material forming the central body 20. Such a greater flexibility of anchor 10 allows reducing the risk of damage to the tissue of the interatrial septum or wall 93. The greater rigidity of the central body 20, instead, enables the central body to maintain a certain radial force outwards, against the walls of septum 93, thus decreasing the risk of displacement or migration of the endoluminal device 100.

In addition, the total surface of the endoluminal device 100 is carefully prepared so as to eliminate any surface imperfection that could increase the formation of thrombi.

Preferably, the endoluminal device 100 comprises a plurality of radiopaque markers, used to easily identify the ends of the endoluminal device 100 with non-invasive techniques, such as X-ray or ultrasound, during or after the procedure. Preferably, the markers are applied to anchors 10.

The central body 20 is adapted to be positioned within a hole present in the interatrial septum or wall 93 of the heart.

Figure 3:
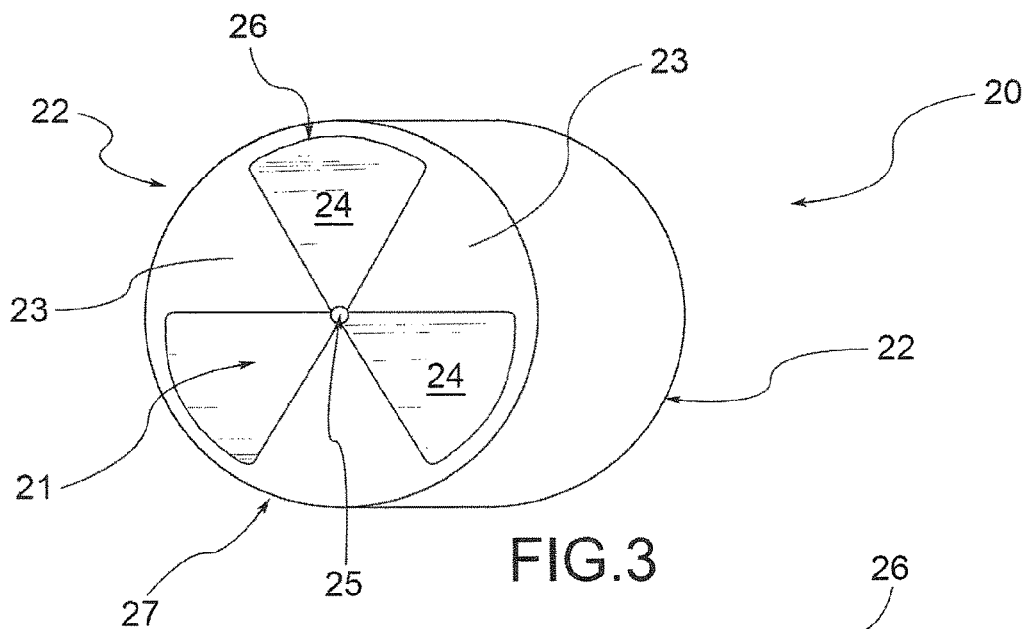
FIG. 3 shows an axonometric view of a component, in particular of the central body 20, of an endoluminal device according to the present invention, according to one embodiment variant.

In the embodiment variant shown in FIG. 3, the central body 20 is cylindrical and includes an inner lumen 21 adapted to allow the passage of interatrial blood.

Figure 4:
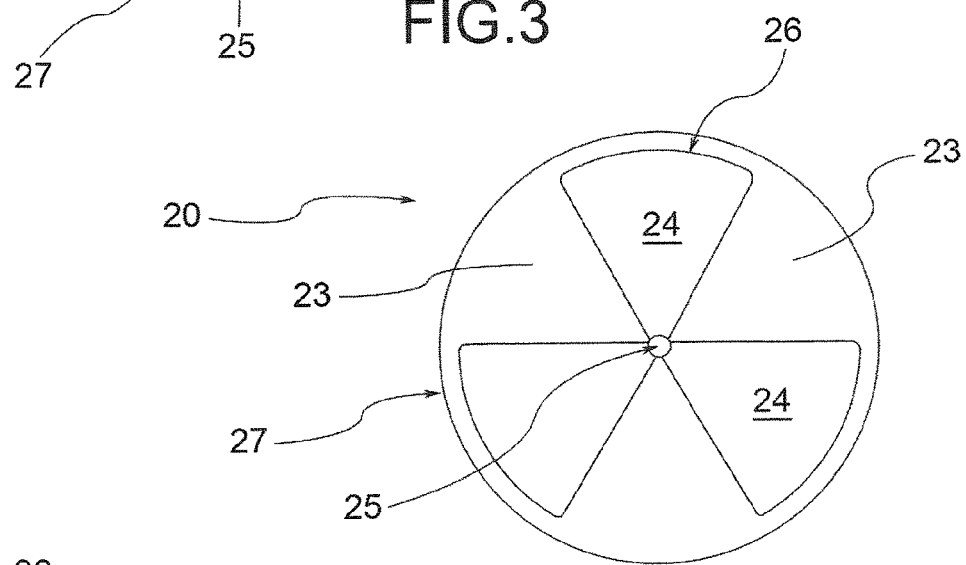
FIG. 4 shows a front view of a component, in particular of the central body 20, of an endoluminal device according to the present invention, according to a further embodiment variant.

In the embodiment shown in FIG. 4, the central body 20 is substantially a disc.

The central body comprises a plurality of fixed vanes 23, attached to the central body 20 at the circumference 27 and attached to each other at centre 25 of circumference 27.

In the examples in FIGS. 3 and 4, the central body 20 comprises three fixed vanes 23, preferably triangular in shape, each with the base attached to circumference 27 and with the apex attached at centre 25.

Apertures 24 are defined between the fixed vanes 23 that allow the passage of interatrial blood. Preferably, apertures 24 are alternated with the fixed vanes 23.

Preferably, the central body 20 comprises a circular rim 26, which extends in a radial direction from circumference 27 towards centre 25.

In the embodiment variant in FIG. 3, the central body 20 comprises fixed vanes 23 at at least one of ends 22.

The control element 30 is substantially a screw.

The control element 30 comprises a plurality of rotating vanes 33, attached to each other at centre 35 of the control element 30. Preferably, the number of rotating vanes 33 corresponds to the number of apertures 24.

Figure 5:
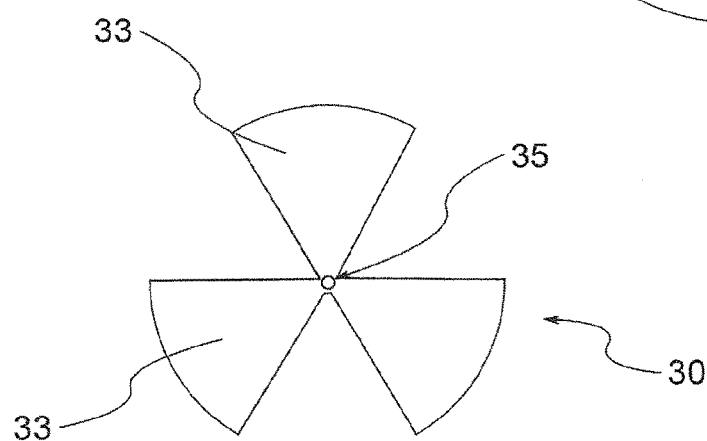
FIG. 5 shows a front view of a component, in particular of the control body 30, of an endoluminal device according to the present invention.

In the embodiment examples in FIG. 5, the control element 30 comprises three rotating vanes 33, preferably triangular in shape, each with the base facing outwards and the apex attached at centre 35.

Figure 6A:
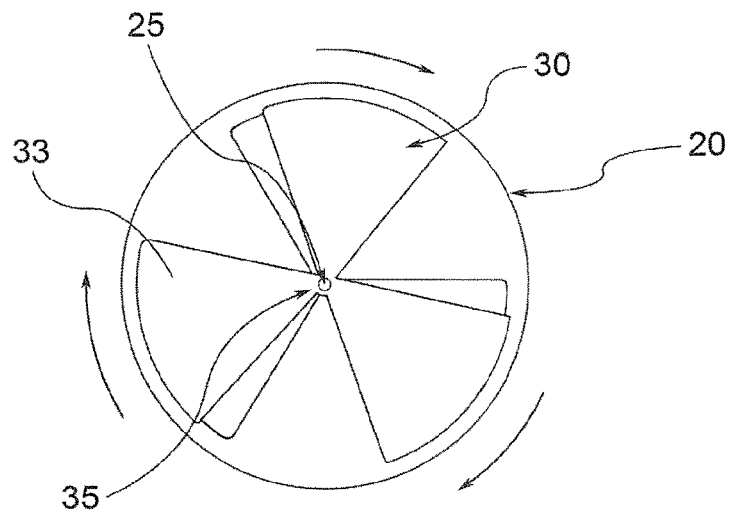
FIGS. 6A and 6B show the operation of an endoluminal device for the control of interatrial blood according to the present invention.
Figure 6B:
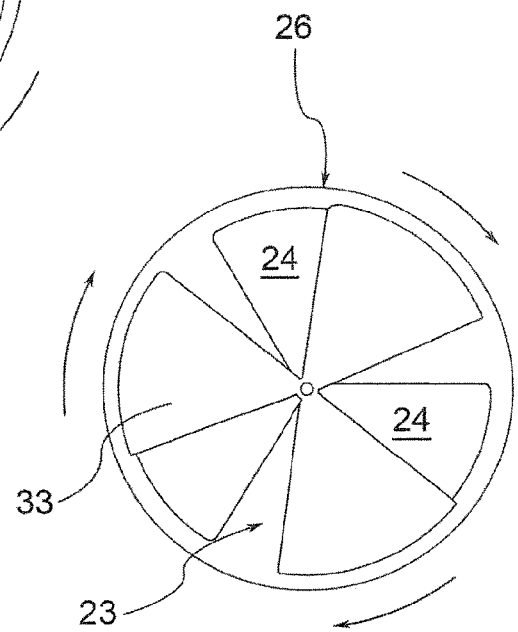

The control element 30 is rotatably engaged on the central body 20 (FIGS. 6A and 6B). In particular, centre 35 of the control element 30 is connected to centre 25 of the central body 20.

The rotation of the control element 30 in relation to the central body 20 provides for a controlled two-way flow of interatrial blood. The interatrial blood flow may be achieved through a single control element 30 (thus through a single propeller) or through a pair of control elements 30 (thus through two propellers rotating in opposite directions). The rotation of the control element 30 relative to body 20 provides a forced two-way flow of interatrial blood from right to left or from left to right, depending on the hemodynamic needs. In particular, the control element 30 operates depending on the pressure gradient between the right atrium and the left atrium, due to a pressure increase in the atrium in which an unbalance is present. The control element 30 therefore allows mitigating this pressure gradient between the two cavities.

As shown in FIGS. 6A and 6B, the rotation of vanes 33 also allows modifying the free area (apertures 24) for the passage of interatrial blood and thus the amount of blood flow between the right atrium and the left atrium. Moreover, when the control element 30 is not rotating, apertures 24 provided on body 20 can be fully closed, thus preventing the circulation of interatrial blood.

As can be seen in FIGS. 6A and 6B, the circular rim 26 allows reducing the blood losses between the control element 30 (and in particular between the rotating vanes 33) and the central body 20.

Both the central body 20 and the control element 30 are made with flexible materials (e.g. metal alloy, with the same materials described in relation to anchors 10), so as to be bendable and foldable to be mounted on a specific delivery catheter or delivery system.

Figure 7A:
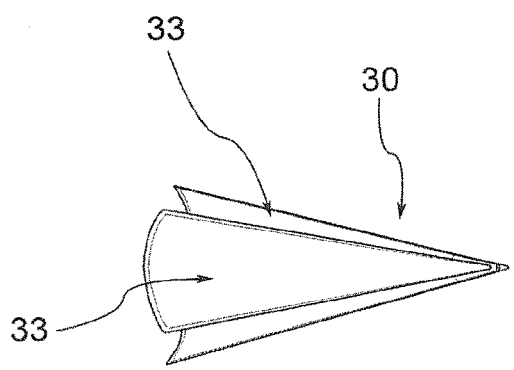
FIGS. 7A and 7B show the endoluminal device according to the present invention, folded for loading on a delivery catheter.
Figure 7B:
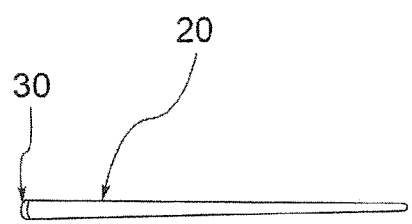

In particular, in embodiments in which the central body 20 is substantially a disc and the control element 30 is substantially a propeller, both components 20 and 30 may be folded (as shown in FIGS. 7A and 7B) in order to make the endoluminal device 100 easily insertable in the inner lumen of a delivery catheter.

The present invention also relates to an endoluminal system for the treatment of heart failure, and in particular for the control of interatrial blood for the creation of a controlled two-way flow. Such a system comprises:
- an endoluminal device 100 comprising at least one control element 30 adapted to create a controlled two-way flow of interatrial blood;
- a release catheter for the transport and positioning of the endoluminal device 100 inside the patient's heart;
- an electric motor for operating the control element 30;
- an energy transmission device to power the motor;
- at least one pressure sensor for the continual measurement of the blood pressure in the right and left atrium;
- a control unit for processing the information relating to pressure and to the endoluminal system 100 (such as speed and direction of rotation of the control element 30) and for the regulation of the interatrial two-way blood flow;
- a data transmission device, for data transmission between the sensor, control unit and motor.

As discussed above, the endoluminal device 100 is adapted to be compressed to a substantially cylindrical shape to be fitted onto a delivery catheter for placement within the patient's heart. Such a delivery is provided with at least one inner lumen, for example to accommodate a guidewire or for the injection of contrast fluid or other substances, or for measuring the pressure at the distal end of the catheter. For example, the central lumen is adapted to accommodate a 0.018" or 0.035" guidewire. In an embodiment variant, the delivery catheter is an "over the wire" catheter in which the inner lumen for the guidewire extends over the entire length of the catheter. In a further embodiment variant, the delivery catheter is a "rapid exchange" catheter with a first inner lumen which extends over the entire length of the catheter and an extra lumen, for sliding the guidewire, which extends only in a distal portion of the catheter, and in particular from the distal end to a lateral hole (or exit port) provided on the catheter.

The endoluminal system further comprises an electric motor for operating the control element 30; Preferably, the motor is an electric motor with permanent magnet rotor which works through electromagnetic induction and therefore needs no power through metal cables. Also the motor is sized so that it can be placed within a delivery catheter.

The endoluminal system also includes a power transmission device and a data transmission device. In an embodiment variant, both the power transmission device that the data transmission device are separate components of the endoluminal device 100. For example, such transmission devices are an ICD (implantable cardioverter defibrillator) or CRT (cardiac resynchronization therapy) positioned using a special catheter (e.g. as described in European patent EP0769308B1).

The endoluminal system also includes at least one pressure sensor to continuously measure the blood pressure in the right and left atrium. The pressure information is sent to a special control unit that, through specific algorithms, calculates and sets the speed of rotation of the control element 30 and the direction of rotation.

Preferably, the control unit includes a body, such as of metal, which accommodates batteries, a motherboard (microchip) which manages and processes the data received from the sensors and generates a signal to be sent through a special antenna to the motor of the control element 30.

Preferably, the control unit is positioned in a special pocket created under the patient's skin in the upper chest.

Using special software, it is possible to access information about the endoluminal device 100 (interatrial pressure, rotational speed of the control element 30, direction of rotation of the control element 30) and make changes to the operating algorithms so as to adjust the interatrial two-way flow according to the clinical needs.

Innovatively, an endoluminal device and an endoluminal system for controlling interatrial blood adapted to create a controlled two-way flow, according to the present invention, reduces the high pressure in the right side and in the left side of the heart, thus relieving the symptoms of heart failure and ventricular overload.

Advantageously, an endoluminal device and an endoluminal system according to the present invention allows the control and the regulation of the amount of blood that flows from left to right or from right to left according to the atrial pressure increase above a maximum predetermined limit, with the goal of reducing the rate and severity of pulmonary edema or right ventricular failure.

It should be clear that a person skilled in the art may make certain modifications to endoluminal devices and the endoluminal system described above, and still fall within the scope of protection claimed herein.

The invention claimed is:

1. An endoluminal device comprising:
a central body adapted to permit the passage of interatrial blood;
at least one anchor attached to the central body adapted to keep the endoluminal device in position within a defect in the interatrial septum of a patient's heart; and
at least one control element engaged with the central body in a rotating manner
wherein the rotation of the control element in relation to the central body creates a two-way flow of interatrial blood wherein the control element consists essentially of a propeller comprising a plurality of rotating vanes attached to each other at the center of the control element, and wherein the central body comprises:
a plurality of fixed vanes attached to the central body at its circumference and attached to each other at the center of the circumference; and
a plurality of apertures configured to alternate with the fixed vanes and adapted to permit the passage of interatrial blood.

2. The endoluminal device of claim 1, comprising a pair of control elements rotating in opposite directions.

3. The endoluminal device of claim 1, wherein the number of rotating vanes corresponds to the number of apertures.

4. The endoluminal device of claim 1, wherein the center of the control element is configured to engage in a rotating manner at the center of the central body.

5. The endoluminal device of claim 1, wherein the central body comprises a circular rim which extends in a radial direction from the circumference towards the center.

6. The endoluminal device of claim 1, wherein the central body is cylindrical and is provided with an inner lumen.

7. The endoluminal device of claim 1, wherein the central body consists essentially of a disc.

8. The endoluminal device of claim 1 comprising a pair of anchors, each attached to one end of the central body.

9. The endoluminal device of claim 1, wherein the anchor comprises an open link, or a plurality of flanges which extend radially from the central body.

10. The endoluminal device of claim 1 comprising at least one radiopaque marker applied to the anchor.

11. An endoluminal system for the treatment of heart failure, comprising:
- the endoluminal device of claim 1;
- a release catheter for the transport and positioning of the endoluminal device inside the patient's heart;
- an electric motor for operating the control element;
- an energy transmission device to power the motor;
- at least one pressure sensor for the continual measurement of the blood pressure in the right and left atrium;
- a control unit for regulating the interatrial two-way blood flow; and
- a data transmission device, for data transmission between the sensor, the control unit and motor.

12. The endoluminal system of claim 11, wherein the motor is an electromagnetic induction electric motor.

* * * * *